(12) United States Patent
Gore et al.

(10) Patent No.: US 8,344,168 B2
(45) Date of Patent: Jan. 1, 2013

(54) PROCESS FOR THE PREPARATION OF FLUTICASONE PROPIONATE

(75) Inventors: Vinayak G. Gore, Panvel (IN); Mahesh Gadakar, Panvel (IN); K. Pokharkar, Panvel (IN); V. Wakchure, Panvel (IN)

(73) Assignee: Generics (UK) Limited (GB)

( * ) Notice: Subject to any disclaimer, the term of this patent is extended or adjusted under 35 U.S.C. 154(b) by 797 days.

(21) Appl. No.: 12/329,790

(22) Filed: Dec. 8, 2008

(65) Prior Publication Data
US 2009/0177001 A1 Jul. 9, 2009

Related U.S. Application Data

(63) Continuation of application No. PCT/GB2007/050328, filed on Jun. 11, 2007.

(30) Foreign Application Priority Data

Jun. 14, 2006 (IN) .............................. 937/MUM/2006
Jun. 14, 2006 (IN) .............................. 938/MUM/2006

(51) Int. Cl.
*C07J 3/00* (2006.01)
(52) U.S. Cl. ...................................................... 552/610
(58) Field of Classification Search .................... 552/610
See application file for complete search history.

(56) References Cited

U.S. PATENT DOCUMENTS

| | | | | | |
|---|---|---|---|---|---|
| 2,629,752 | A | * | 2/1953 | Craig et al. .................. | 585/416 |
| 4,335,121 | A | * | 6/1982 | Phillipps et al. .............. | 514/180 |
| 2002/0133032 | A1 | | 9/2002 | Barkalow et al. | |

FOREIGN PATENT DOCUMENTS

| | | |
|---|---|---|
| EP | 1431305 | 6/2004 |
| EP | 1526139 | 4/2005 |
| GB | 2088877 | 6/1982 |
| IL | 109656 | 2/1998 |
| WO | WO 00/38811 | 6/2000 |
| WO | WO 03/066653 | 8/2003 |
| WO | WO 2004/001369 | 12/2003 |
| WO | WO 2004/052912 | 6/2004 |
| WO | WO 2007/0099548 | 9/2007 |

OTHER PUBLICATIONS

Aigbirhio et al., "Automated Radiosynthesis of No-carrier-added [S-fluoromethyl18F]Fluticasone Propionate as a Radiotracer for Lung Deposition Studies with PET.", Journal of Labelled Compounds and Radiopharmaceuticals, vol. XXXIX(7), pp. 567-584, 1997.*
Phillips, et al., "Synthesis and Structure—Activity Relationships in a Series of Antiinflammatory Corticosteroid Analogues, Halomethyl Androstane-17β-carbothioates and 17β-carboselenoates," *J. Med. Chem.*, 1994, vol. 37, pp. 3717-3729.

* cited by examiner

*Primary Examiner* — Barbara P Badio
(74) *Attorney, Agent, or Firm* — Dorsey & Whitney LLP

(57) ABSTRACT

The present invention relates to a process for the preparation of steroidal 17β-carboxylic thioates. More particularly the present invention relates to a convenient and efficient synthesis of steroidal 17β-carboxylic thioates, such as fluticasone propionate I, using soluble mixed fluorides to introduce fluorine by displacing an appropriate leaving group X in compounds II resulting in selective and controlled fluorination. The present invention also relates to intermediates II and their preparation.

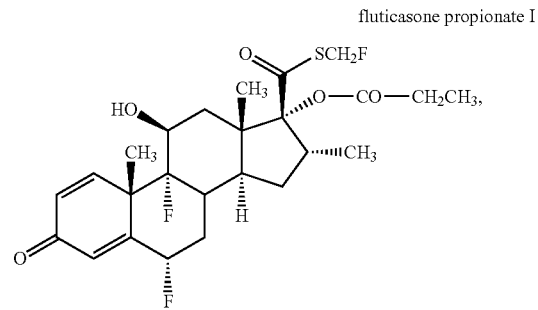

fluticasone propionate I

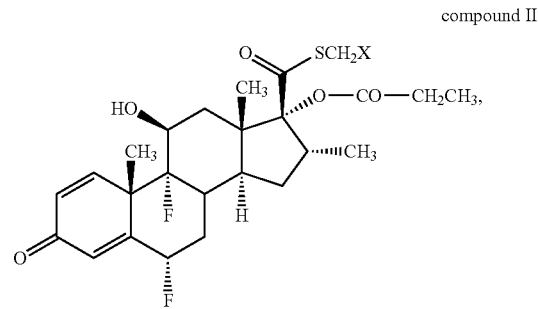

compound II

X = Cl, Br, I, OSO$_2$Ph, OSO$_2$—Ph-pCH$_3$, OSO$_2$CH$_3$, OSO$_2$CF$_3$, OCOCH$_3$

17 Claims, No Drawings

PROCESS FOR THE PREPARATION OF FLUTICASONE PROPIONATE

CROSS-REFERENCE TO RELATED APPLICATIONS

This application is a continuation of International Patent Application No. PCT/GB2007/050328, filed on, Jun. 11, 2007, which claims priority to Indian Application No. 937/mum/2006, filed on Jun. 14, 2006, and Indian Application No. 938/mum/2006, filed on Jun. 14, 2006, the entire contents of both of which are incorporated herein by reference.

FIELD OF THE INVENTION

The present invention relates to a process for the preparation of steroidal 17β-carboxylic thioates. More particularly the present invention relates to a convenient and efficient synthesis of steroidal 17β-carboxylic thioates, such as fluticasone propionate I, using soluble mixed fluorides to introduce fluorine by displacing an appropriate leaving group X in compounds II resulting in selective and controlled fluorination. The present invention also relates to intermediates II and their preparation.

BACKGROUND OF THE INVENTION

Fluticasone propionate I, chemically known as S-fluoromethyl-6α,9α-difluoro-11β-hydroxy-16α-methyl-17α-propionyloxy-3-oxo-androsta-1,4-diene-17β-carbothioate, is a member of the corticosteroidal androstane 17β-thioic acid fluoromethyl ester family and a synthetic steroid of the glucocorticoid family. The naturally occurring hormone, cortisol or hydrocortisone, is produced by the adrenal glands. Glucocorticoid steroids have potent anti-inflammatory actions. When used as a nasal inhaler or spray, the medication goes directly to the inside lining of the nose and very little is absorbed into the rest of the body.

Processes for the synthesis of fluticasone propionate I are known in the prior art, but are associated with various difficulties. For instance, the process disclosed in U.S. Pat. No. 4,335,121, a product patent assigned to Glaxo, starts with flumethasone, where barring the functional groups on C-17 all other required structural features are already in place. The functionalisation of C-17 is achieved by the sequence depicted in scheme 1.

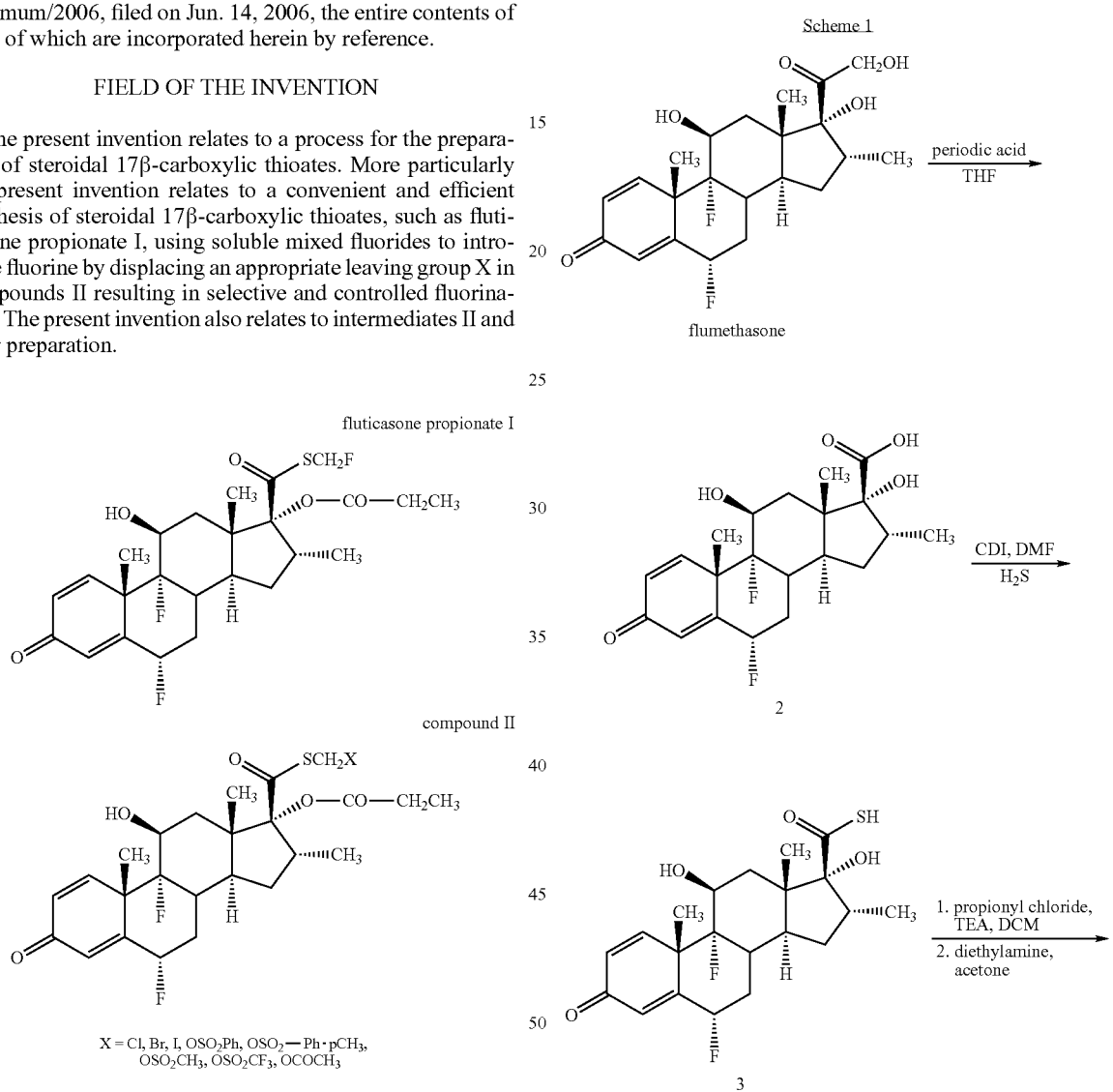

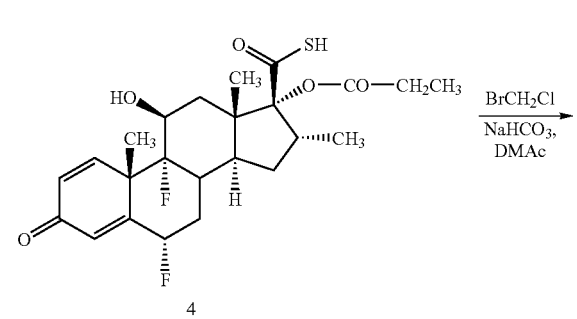

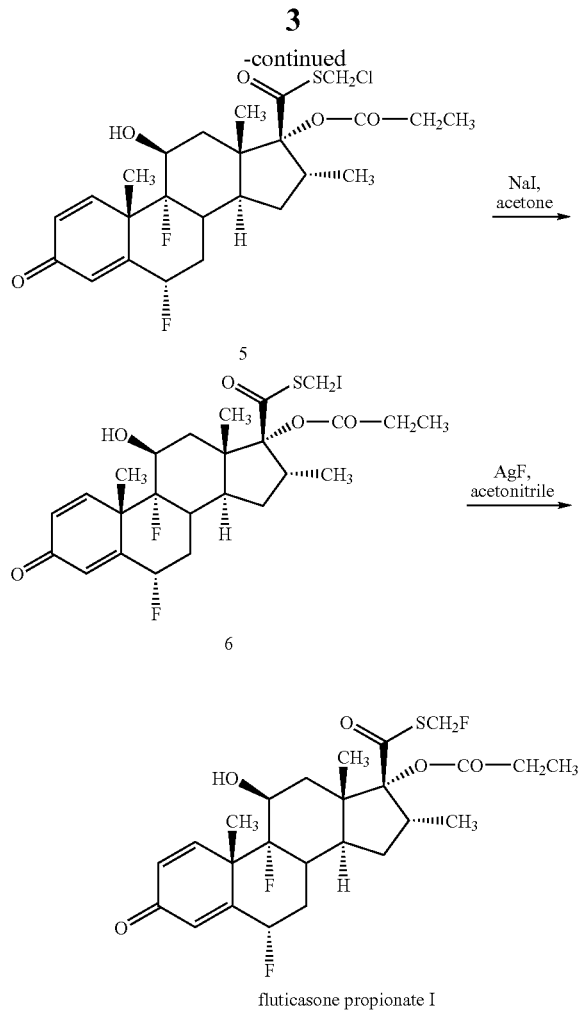

fluticasone propionate I

The first step involved the oxidative cleavage of the hydroxymethyl group on C-17 in flumethasone, which is chemically known as 6α,9α-difluoro-11β,17α,21-trihydroxy-16α-methyl-androsta-1,4-diene-3,20-dione, by periodic acid to obtain 6α,9α-difluoro-11β,17α-dihydroxy-16α-methyl-androsta-1,4-diene-3-one-17β-carboxylic acid 2. Activation of the carboxyl group of compound 2 using N,N'-carbonyldiimidazole (CDI) in dimethylformamide (DMF) and subsequent treatment with $H_2S$ gave 6α,9α-difluoro-11β,17α-dihydroxy-16α-methyl-3-oxo-androsta-1,4-diene-17β-carbothioic acid 3. The C-17 hydroxyl group of compound 3 was esterified using propionyl chloride and triethylamine (TEA) to obtain 6α,9α-difluoro-11β-hydroxy-16α-methyl-17α-propionyloxy-3-oxo-androsta-1,4-diene-17β-carbothioic acid 4. Alkylation of compound 4 with bromochloromethane using $NaHCO_3$ and dimethylacetamide (DMAc) gave S-chloromethyl-6α,9α-difluoro-11β-hydroxy-16α-methyl-17α-propionyloxy-3-oxo-androsta-1,4-diene-17β-carbothioate 5. Halogen exchange with NaI in acetone converted chloromethyl ester 5 into S-iodomethyl-6α,9α-difluoro-11β-hydroxy-16α-methyl-17α-propionyloxy-3-oxo-androsta-1,4-diene-17β-carbothioate 6. In the final step, iodomethyl ester 6 was reacted with silver fluoride (AgF) in acetonitrile to obtain fluticasone propionate I. The chloromethyl ester 5 can also be converted into compound II with X=Br (S-bromomethyl-6α,9α-difluoro-11β-hydroxy-16α-methyl-17α-propionyloxy-3-oxo-androsta-1,4-diene-17β-carbothioate) by using an appropriate nucleophile, such as lithium bromide.

Even though the process described above is eco-friendly, it is not capable of providing fluticasone propionate I sufficiently pure to meet the limits of stringent pharmacopoeial specifications (EP/USP), and the processing conditions for the conversion of chloromethyl ester 5 to iodomethyl ester 6 and then to fluticasone propionate I are very tedious and inefficient.

Specifically, the conversion of chloromethyl ester 5 to iodomethyl ester 6 disclosed in U.S. Pat. No. 4,335,121 suffers from following limitations:

Traces of chloromethyl ester 5 starting material remain even after long reaction times (more than 48 hours). These traces are carried through to subsequent stages up to fluticasone propionate I. The traces of chloromethyl ester 5 are difficult to remove by multiple crystallisations or even by chromatographic separation due to the ester's poor solubility in most polar as well as non-polar solvents.

The conversion of chloromethyl ester 5 to iodomethyl ester 6 suffers from the generation of oxidative degradation impurities. Sulphur compounds 4, 5 and 6 are prone to oxidative dimerisation, and dimer impurities like compounds 11 and 12 were observed at higher temperatures (more than 60° C.) or with longer reaction times. It was observed that such by-products are formed in significant amounts, which are difficult to control/reduce within the limits of stringent pharmacopoeial specifications (EP/USP) even after multiple purifications.

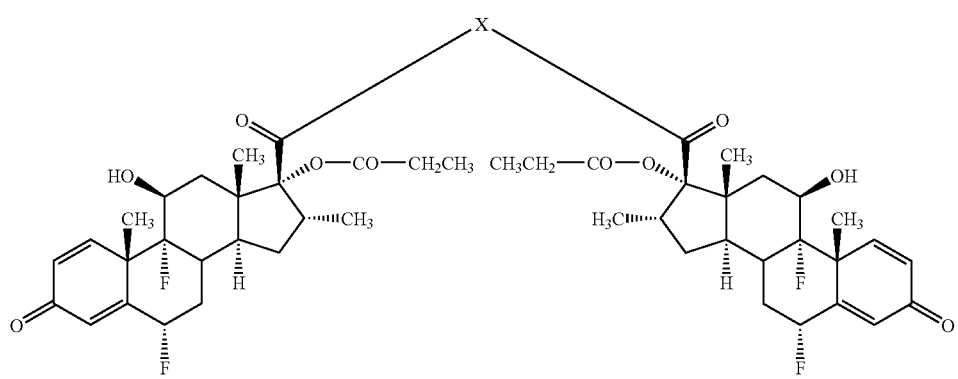

Compound 11: X=—S—S—[17,17'-(disulphanediyldicarbonyl)bis(6α,9α-difluoro-11β-hydroxy-16α-methyl-3-oxo-androsta-1,4-diene-17α-yl)dipropionate]

Compound 12: X=—S—S—S—[17,17'-(trisulphanediyl-dicarbonyl)bis(6α,9α-difluoro-11β-hydroxy-16α-methyl-3-oxo-androsta-1,4-diene-17α-yl)dipropionate]

The conversion of iodomethyl ester 6 to fluticasone propionate I disclosed in U.S. Pat. No. 4,335,121 suffers from the following limitations:

The reaction takes a long time (72 hours-11 days).

An excess of silver fluoride (10-15 eq) must be used for complete conversion, which causes problems during recovery of the silver fluoride from the waste stream.

Because of the excess of silver fluoride used, a thick black insoluble residue forms, which interferes in the homogeneity of the reaction.

The black suspended metallic particles cannot be eliminated easily by Kieselguhr filtration, where these impurities are carried forward even after multiple filtrations. The black metallic impurities require multiple washings with 2M HCl for complete removal.

In the end, after all the tedious aqueous work up, isolation of the product requires preparative chromatography and two crystallisations to obtain material complying with the pharmacopoeial limits. This chromatographic purification further limits the applicability of this process on a commercial scale.

According to Israeli patent application IL 109656, fluticasone propionate I was synthesized directly from 6α,9α-difluoro-11β-hydroxy-16α-methyl-17α-propionyloxy-3-oxo-androsta-1,4-diene-17β-carbothioic acid 4 using a halofluoromethane, for example bromofluoromethane, and phase transfer catalysts, as shown in scheme 2. The disadvantage of this process is the use of halofluoromethanes, such as bromofluoromethane, which are non-eco-friendly reagents known to damage the ozone layer of the atmosphere.

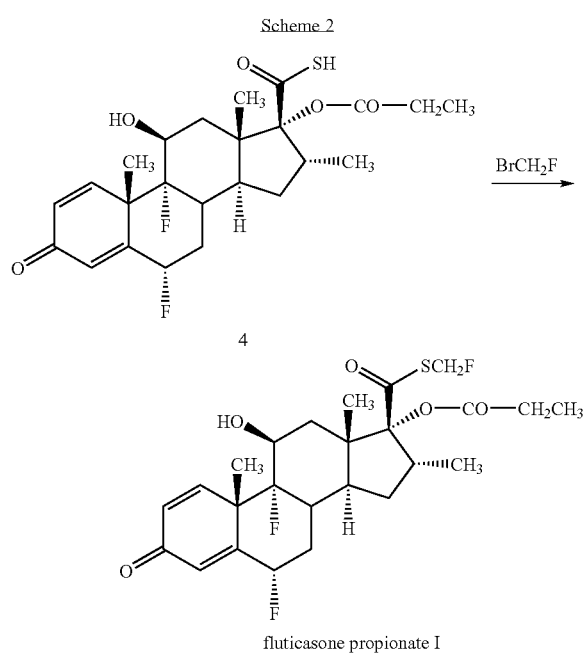

The process described in international patent application WO 2004/001369 involves the following steps depicted in scheme 3.

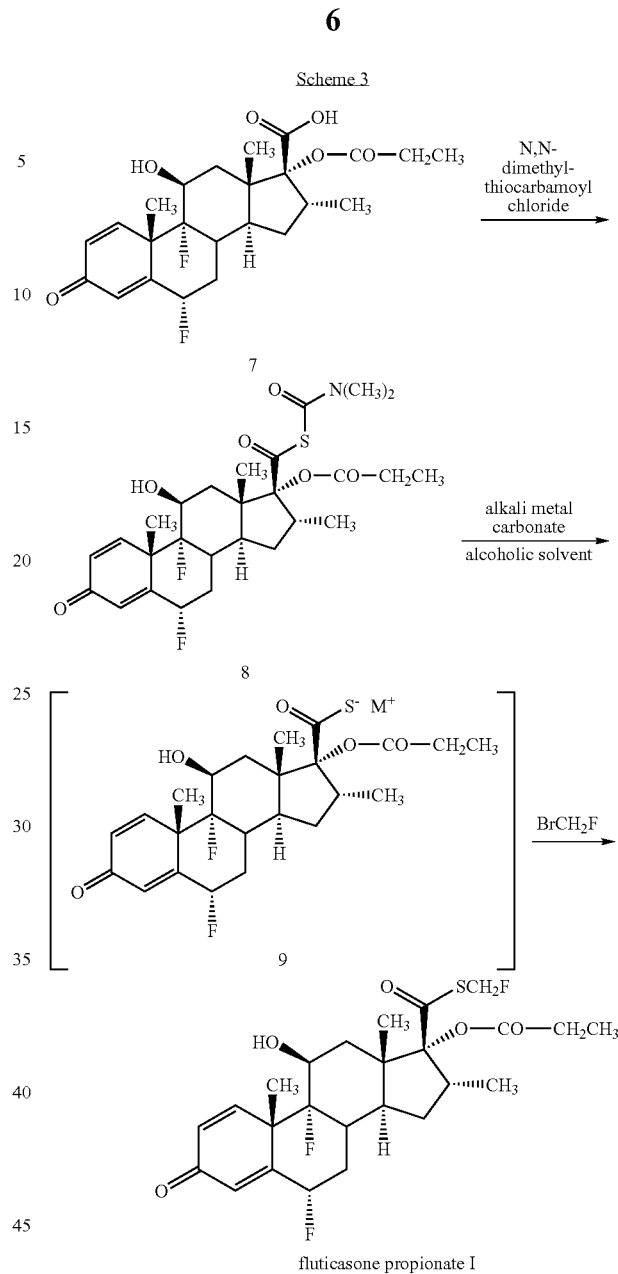

6α,9α-Difluoro-11β-hydroxy-16α-methyl-17α-propionyloxy-3-oxo-androsta-1,4-diene-17β-carboxylic acid 7 was converted into the corresponding thiocarbamate 8 using N,N-dimethylthiocarbamoyl chloride in an inert aprotic solvent in the presence of an iodide catalyst and a base. The 17β-N,N-dimethylthiocarbamoyloxycarbonyl compound 8 was treated with an alkali metal carbonate-alcohol system, for example potassium carbonate in methanol, to obtain the alkali metal salt 9 of compound 4 (6α,9α-difluoro-11β-hydroxy-16α-methyl-17α-propionyloxy-3-oxo-androsta-1,4-diene-17β-carbo-thioate sodium). Alkali metal salt 9 was treated in situ with bromofluoromethane to obtain fluticasone propionate I. Alternatively, compound 4 was isolated by acid treatment and then reacted with bromofluoromethane to obtain fluticasone propionate I. Alternatively still, thiocarbamate 8 was reacted with a hydrosulphide reagent, such as sodium hydrosulphide, and bromofluoromethane to obtain fluticasone propionate I. Hence, this process also uses bromofluoromethane, which raises environmental concerns.

US patent application USSN 2002/0133032 by Abbot Laboratories also discloses the hydrolysis of compound 8 with sodium hydrosulphide to generate alkali metal salt 9, which was then treated in situ with chlorofluoromethane to obtain fluticasone propionate I.

The process disclosed in European patent application EP 1431305 comprises the following steps. Organic amine salts of 6α,9α-difluoro-11β-hydroxy-16α-methyl-17α-propionyloxy-3-oxo-androsta-1,4-diene-17β-carbothioic acid 10 were prepared with different aliphatic amines in isopropanol as a preferred solvent. The isolated organic amine salt 10 was further reacted with chlorofluoromethane in acetonitrile as a preferred solvent at 50° C. in a closed vessel at a pressure of ~1.3 bar to afford fluticasone propionate I as shown in scheme 4.

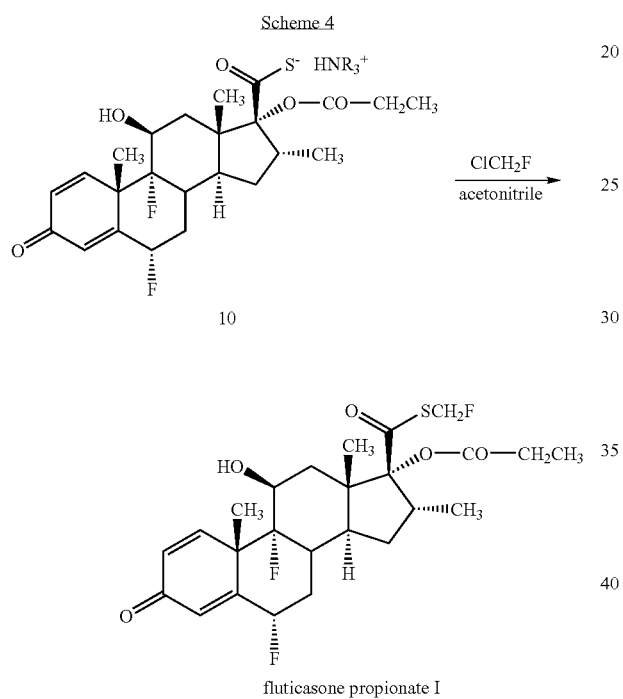

Although the process described in EP 1431305 is capable of producing relatively pure fluticasone propionate I, a drawback associated with this process is the oxidative dimerisation of the sulphur compounds to give dimer impurities 11 and 12, especially under pressure or with long reaction times. Such by-products are formed in significant amounts, which are difficult to control/reduce within the limits of stringent pharmacopoeial specifications even after multiple purifications.

A process disclosed by Farmabios in international patent application WO 2004/052912 used a different approach, shown in scheme 5, for the conversion of organic amine salt 4 to fluticasone propionate I. Amine salt 4 was hydroxymethylated using formaldehyde to give alcohol 13 (S-hydroxymethyl-6α,9α-difluoro-11β-hydroxy-16α-methyl-17α-propionyloxy-3-oxo-androsta-1,4-diene-17β-carbothioate). This intermediate 13 was selectively fluorinated using bis(2-methoxyethyl)aminosulphur trifluoride (DEOXO-FLUOR®), diethylaminosulphur trifluoride (DAST®), or hexafluoropropyldiethylamine (MEC-81®), to obtain fluticasone propionate I.

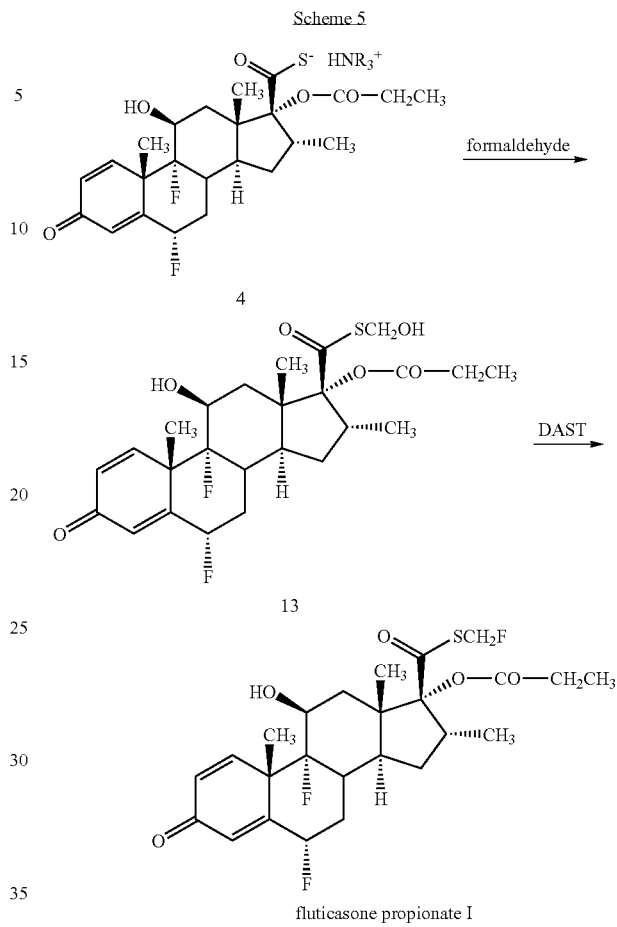

WO 2004/052912 also discloses a minor modification of the process described in scheme 5. In the modified process, depicted in scheme 6, 17β-N,N-dimethylthiocarbamoyloxycarbonyl-9β,11β-epoxy-6α-fluoro-17α-propionyloxy-16α-methyl-3-oxo-androsta-1,4-diene 14 was converted to S-hydroxymethyl-9β,11β-epoxy-6α-fluoro-17α-propionyloxy-16α-methyl-3-oxo-androsta-1,4-diene-carbothioate 15. Intermediate 15 was further converted into S-fluoromethyl-9β,11β-epoxy-6α-fluoro-17α-propionyloxy-16α-methyl-3-oxo-androsta-1,4-diene-carbothioate 16 using DAST®. Fluticasone propionate I was then obtained by the opening of the epoxide of compound 16 using hydrofluoric acid. The use of hazardous DAST® as a fluorinating agent and the use of highly corrosive hydrofluoric acid are major disadvantages of this process described in WO 2004/052912.

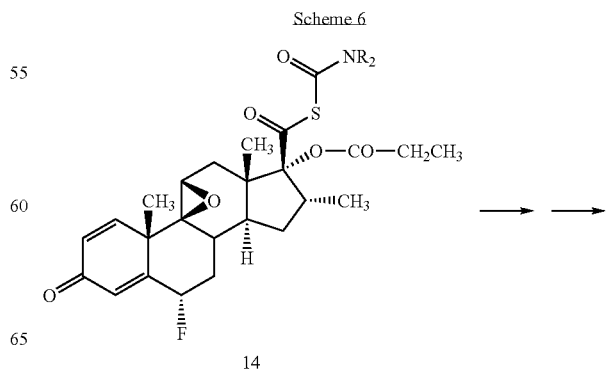

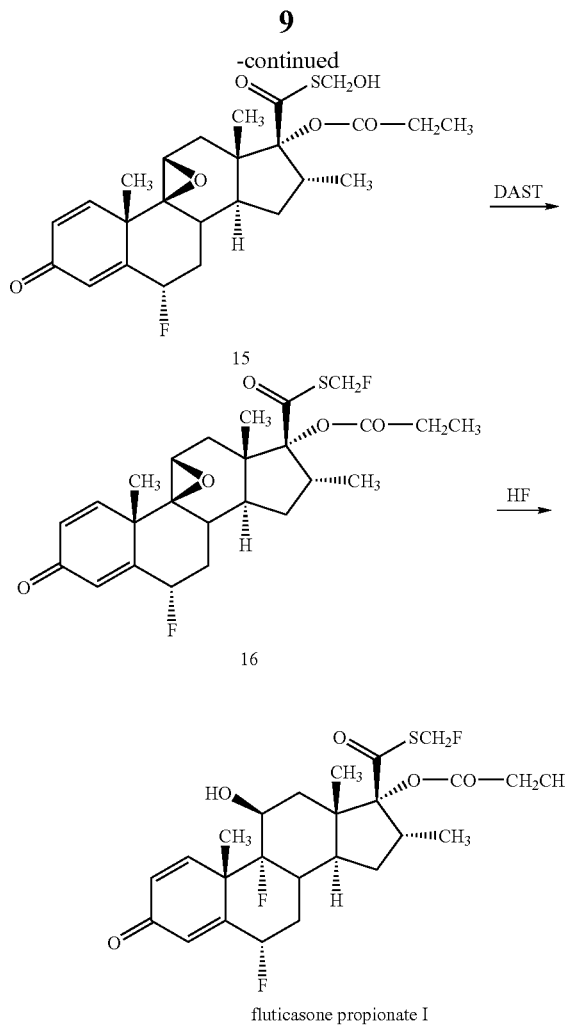

fluticasone propionate I

Thus the prior art processes described above for the synthesis of fluticasone propionate I suffer from various limitations with respect to process parameters, yields, purity and quality, as well as serious environmental issues due to the use of halofluoromethanes. In view of these drawbacks, there is a need for an improved process for the preparation of fluticasone propionate I, which addresses the limitations associated with the prior art processes.

Moreover, thioalkyl derivatives II are very sensitive towards oxidative as well as free radical dimerisation at temperatures of more than 60° C. and by prolonged heating. The present inventors converted iodomethyl ester 6, obtained following the process disclosed in U.S. Pat. No. 4,335,121, into fluticasone propionate I. Even after numerous attempts it was found that the required quality of fluticasone propionate I could not be obtained, unless iodomethyl ester 6 was purified to a certain level before its conversion into fluticasone propionate I. Hence, the purification of iodomethyl ester 6 was essential to obtain fluticasone propionate I of the required quality. However, the purification of this key intermediate, i.e. iodomethyl ester 6, is not disclosed in any of the literature, and in particular not in U.S. Pat. No. 4,335,121.

In addition, iodomethyl ester 6, the dimer impurities and other non-polar related impurities have poor solubility in polar as well as non-polar solvents and therefore the purification of iodomethyl ester 6 by crystallisation or chromatographic separation becomes very tedious and uneconomic. The poor solubility of iodomethyl ester 6, the dimer impurities and other non-polar related impurities also hinders the next step, the synthesis of fluticasone propionate I, where multiple crystallisations as well as chromatographic purifications are required to achieve the pharmacopoeial limits of these impurities (0.3-0.4%).

In view of these problems, there is also a need to develop an improved process for the preparation and purification of the key intermediates, thioalkyl derivatives II, in the preparation of fluticasone propionate I, which addresses the limitations associated with the prior art processes.

OBJECTS OF THE INVENTION

Therefore, it is an object of the present invention to provide a process for the preparation of fluticasone propionate I conforming to EP/USP specifications (EP 5.0 or USP 29).

It is a further object of the present invention to provide a convenient and efficient synthesis of fluticasone propionate I using soluble mixed fluorides resulting in selective and controlled fluorination.

Another object of the present invention is to provide a process for the preparation of fluticasone propionate I, which is convenient for commercial scale production and does not involve any tedious operations such as chromatographic separation.

Another object of the present invention is to develop an eco-friendly and economical process for the preparation of fluticasone propionate I, comprising the use of non-hazardous reagents for the introduction of fluorine.

Another object of the present invention is fluticasone propionate I with low levels of impurities, particularly dimer impurities.

Another object of the present invention is fluticasone propionate I, comprising non-polar impurities, such as dimer impurities 11 and 12, in an amount of less than the pharmacopoeial limits (EP 5.0 or USP 29).

Another object of the present invention is to provide fluticasone propionate I as per EP/USP specifications (EP 5.0 or USP 29).

Yet another object of the present invention is to provide a process for the preparation of thioalkyl intermediates II, which can be used in the preparation of fluticasone propionate I, using radical inhibitors and/or antioxidants during their preparation.

Another object of the present invention is to provide a suitable methodology/purification method (crystallisation from suitable solvent(s)) to achieve the required quality of thioalkyl intermediates II, when their preparation process does not afford the required quality in some instances.

SUMMARY OF THE INVENTION

According to a first aspect of the present invention there is provided a process using soluble mixed fluorides for selective and controlled fluorination to obtain high quality fluticasone propionate I.

The first aspect of the present invention provides a process of preparing S-fluoromethyl-6α,9α-difluoro-11β-hydroxy-16α-methyl-17α-propionyloxy-3-oxo-androsta-1,4-diene-17β-carbothioate I

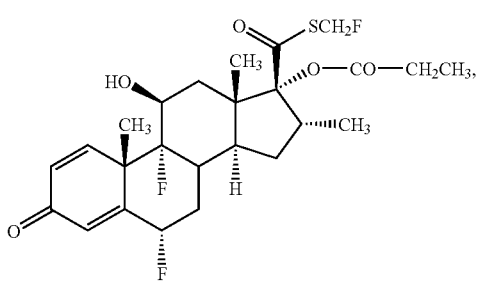

comprising using soluble mixed fluorides to fluorinate a compound II wherein X is a leaving group.

The leaving group X may be, for example, a chloro, bromo, iodo, benzenesulphonyl, p-toluenesulphonyl(tosyl), methylsulphonyl(mesyl), trifluoromethanesulphonyl(triflate), or acetyl group. Preferably, the leaving group X is a bromo, iodo, benzenesulphonyl, p-toluenesulphonyl(tosyl), methylsulphonyl(mesyl), trifluoromethanesulphonyl(triflate), or acetyl group. Preferably, the leaving group X is iodo.

As used herein, the term 'soluble mixed fluorides' means at least two fluorides, which are soluble at least to some extent in the reaction solvent used. The reaction solvent may be an organic solvent. The organic solvent may be selected from, for example, acetonitrile, tetrahydrofuran, ethyl acetate, dimethylformamide, dimethylacetamide, and a combination of ethyl acetate and acetonitrile, benzonitrile or propionitrile. Preferably, the organic solvent comprises or is acetonitrile.

The soluble mixed fluorides may be selected from, for example, potassium fluoride, caesium fluoride, antimony fluoride, tetrabutyl ammonium fluoride, calcium fluoride, silver fluoride, bis(2-methoxyethyl)aminosulphur trifluoride (DEOXO-FLUOR®), diethylamino-sulphur trifluoride (DAST®), and hexafluoropropyldiethylamine (MEC-81®). Preferably, the soluble mixed fluorides are selected from potassium fluoride, caesium fluoride, antimony fluoride, tetrabutyl ammonium fluoride, calcium fluoride, and silver fluoride.

In a preferred embodiment of the present invention, the soluble mixed fluorides comprise silver fluoride and at least one other fluoride. Preferably, the soluble mixed fluorides comprise or are silver fluoride and calcium fluoride.

The soluble mixed fluorides may be a solution of soluble mixed fluorides in an organic solvent. Preferably, the soluble mixed fluorides are a solution of silver fluoride and calcium fluoride in an organic solvent. Preferably, the solution of soluble mixed fluorides is prepared by heating the soluble mixed fluorides in the organic solvent at a temperature of 25-95° C., preferably at a temperature of 50-95° C., preferably at about the reflux temperature of the organic solvent. The organic solvent may be selected from, for example, acetonitrile, tetrahydrofuran, ethyl acetate, dimethylformamide, dimethylacetamide, and a combination of ethyl acetate and acetonitrile, benzonitrile or propionitrile. Preferably, the organic solvent comprises or is acetonitrile.

Preferably, the use of the soluble mixed fluorides results in selective and controlled fluorination of the —CO—SCH$_2$X group of compound II.

The process of the first aspect of the present invention may further comprise the step of crystallising compound I from an alcohol, such as ethanol or methanol, preferably methanol.

Preferably, the compound I obtained comprises less than 0.4% non-polar dimer impurities 11 and 12, preferably less than 0.3%, preferably less than 0.2%, preferably less than 0.1%. Preferably, the compound I obtained comprises less than 0.2% non-polar dimer impurities 11 and 12 each, preferably less than 0.1% each.

Preferably, the HPLC purity of the compound I obtained is greater than 97%, preferably greater than 98%, preferably greater than 99%, preferably greater than 99.5%, preferably greater than 99.7%.

Preferably, the yield of the compound I obtained is greater than 60%, preferably greater than 70%, preferably greater than 75%, preferably greater than 80%, preferably greater than 85%.

A second aspect of the present invention provides S-fluoromethyl-6α,9α-difluoro-11β-hydroxy-16α-methyl-17α-propionyloxy-3-oxo-androsta-1,4-diene-17β-carbothioate I, when obtained by a process of the first aspect of the present invention.

The second aspect of the present invention also provides S-fluoromethyl-6α,9α-difluoro-11β-hydroxy-16α-methyl-17α-propionyloxy-3-oxo-androsta-1,4-diene-17β-carbothioate I, which has an HPLC purity of greater than 99%, preferably greater than 99.5%, preferably greater than 99.7%.

According to a third aspect of the present invention there is provided a process of purifying a thioalkyl intermediate II by crystallisation using non-polar and polar solvents to control the amount of non-polar dimer and oxidative impurities.

The third aspect of the present invention provides a process of purifying a compound II wherein X is a leaving group, comprising crystallising compound II using a solvent system comprising a polar and a non-polar solvent.

The leaving group X may be, for example, a bromo, iodo, benzenesulphonyl, p-toluenesulphonyl (tosyl), methylsulphonyl(mesyl), trifluoromethanesulphonyl(triflate), or acetyl group. Preferably, the leaving group X is iodo or bromo, more preferably iodo.

As used herein, 'non-polar' solvents include, but are not limited to, methyl acetate, ethyl acetate, isopropyl acetate, butyl acetate, acetone, THF, dimethylformamide, and dimethylacetamide. As used herein, 'polar' solvents include, but are not limited to, formic acid, acetic acid, propionic acid, butyric acid, and methanol. The non-polar/polar solvent system may comprise, for example, methyl acetate/formic acid, methyl acetate/acetic acid, ethyl acetate/acetic acid, isopropyl acetate/acetic acid, butyl acetate/acetic acid, ethyl acetate/propionic acid, or ethyl acetate/butyric acid. Preferably, the solvent system comprises ethyl acetate and acetic acid, preferably in an ethyl acetate:acetic acid ratio of about 1:2.

Preferably, the compound II obtained comprises less than 0.4% non-polar dimer impurities 11 and 12, preferably less than 0.3%, preferably less than 0.2%, preferably less than 0.1%. Preferably, the compound II obtained comprises less than 0.2% non-polar dimer impurities 11 and 12 each, preferably less 0.1% each.

Preferably, the HPLC purity of the compound II obtained is greater than 95%, preferably greater than 97%, preferably greater than 98%, preferably greater than 99%, preferably greater than 99.5%.

Preferably, the yield of the compound II obtained is greater than 60%, preferably greater than 70%, preferably greater than 80%, preferably greater than 85%, preferably greater than 90%.

According to a fourth aspect of the present invention there is provided a process of preparing a thioalkyl intermediate II, comprising converting a thioalkyl intermediate III into thioalkyl intermediate II in the presence of a radical inhibitor and/or an antioxidant to control the amount of non-polar dimer and oxidative impurities.

The fourth aspect of the present invention provides a process of preparing a compound II

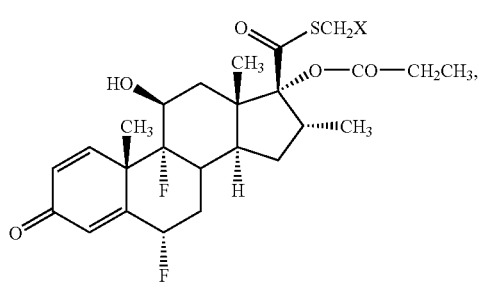

wherein X is a leaving group, comprising converting a compound III

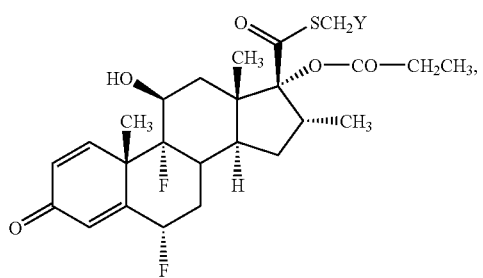

wherein Y is another leaving group, into compound II in the presence of a radical inhibitor or an antioxidant or both.

The leaving group X may be, for example, a bromo, iodo, benzenesulphonyl, p-toluenesulphonyl (tosyl), methylsulphonyl(mesyl), trifluoromethanesulphonyl(triflate), or acetyl group. Preferably, the leaving group X is iodo or bromo, preferably iodo.

The leaving group Y may be, for example, a chloro, bromo or hydroxyl group. Preferably, the leaving group Y is chloro.

Leaving groups X and Y are not the same. Preferably, if Y is chloro, then X is bromo or iodo, preferably iodo. Preferably, if Y is bromo, then X is iodo. Preferably, if Y is a hydroxyl group, then X is a sulphonyl or acetyl group.

The radical inhibitor may be selected from, for example, methylhydroquinone, bis(4-methoxy-3-tert-butyl-5-methylphenyl)sulphide, cyclohexene, L-cysteine, N,N-dimethylglycine, sorbic acid and hydroquinone. Preferably, the radical inhibitor is hydroquinone.

The antioxidant may be selected from, for example, ascorbic acid, potassium metabisulphite, sodium metabisulphite, sodium thiosulphate, butylated hydroxyanisole and butylated hydroxytoluene. Preferably, the antioxidant is butylated hydroxytoluene.

Preferably, the conversion is carried out in presence of hydroquinone and butylated hydroxytoluene.

Preferably, the compound II obtained comprises less than 0.5% non-polar dimer impurities 11 and 12, preferably less than 0.4%, preferably less than 0.3%. Preferably, the compound II obtained comprises less than 0.3% non-polar dimer impurities 11 and 12 each, preferably less than 0.2%.

Preferably, the HPLC purity of the compound II obtained is greater than 95%, preferably greater than 96%, preferably greater than 97%.

Preferably, the yield of the compound II obtained is greater than 60%, preferably greater than 70%, preferably greater than 80%, preferably greater than 85%, preferably greater than 90%.

Preferably, compound II, obtained by a preparation process according to the fourth aspect of the present invention, is further purified by a purification process according to the third aspect of the present invention.

Preferably, compound II, obtained by a preparation process according to the fourth aspect of the present invention and/or by a purification process according to the third aspect of the present invention, is further converted into compound I by a process according to the first aspect of the present invention.

A fifth aspect of the present invention provides a compound II

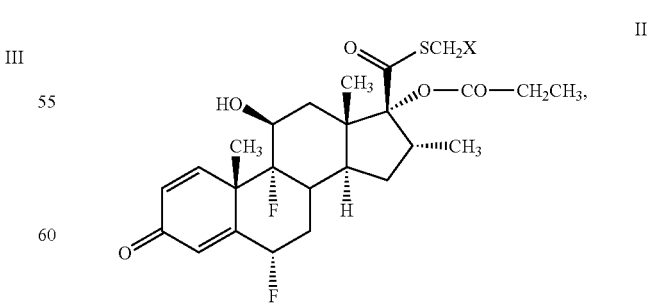

wherein X is a leaving group, when obtained by a process according to the third and/or fourth aspect of the present invention.

The fifth aspect of the present invention also provides a compound II

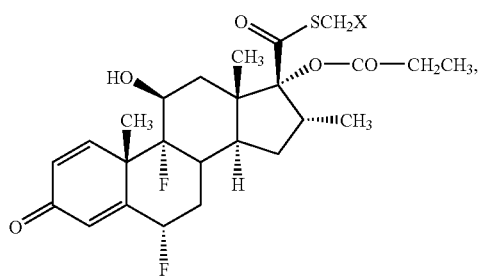

II wherein X is a leaving group, which has an HPLC purity of greater than 95%, preferably greater than 97%, preferably greater than 98%, preferably greater than 99%, preferably greater than 99.5%.

The leaving group X may be, for example, a bromo, iodo, benzenesulphonyl, p-toluenesulphonyl (tosyl), methylsulphonyl(mesyl), trifluoromethanesulphonyl(triflate), or acetyl group. Preferably, the leaving group X is iodo or bromo, preferably iodo.

Any of the processes of the present invention can be carried out on an industrial scale, for example, to manufacture compound I or compound II in batches of 50 g, 100 g, 500 g, 1 kg, 5 kg, 10 kg, 50 kg, 100 kg or more.

DETAILED DESCRIPTION OF THE INVENTION

The present invention relates to the preparation of fluticasone propionate I which complies with the pharmacopoeial limits EP 5.0 or USP 29). The present inventors have found several process improvements, which can be implemented separately or simultaneously, which increase the purity of fluticasone propionate I compared to prior art preparation processes. The improvements relate to the following two preparation steps (a) and (b):

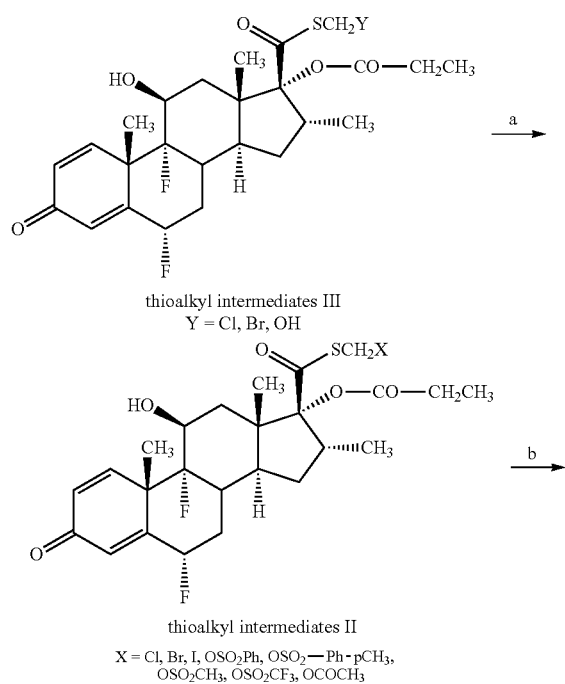

thioalkyl intermediates III
Y = Cl, Br, OH thioalkyl intermediates II
X = Cl, Br, I, OSO$_2$Ph, OSO$_2$—Ph-pCH$_3$, OSO$_2$CH$_3$, OSO$_2$CF$_3$, OCOCH$_3$

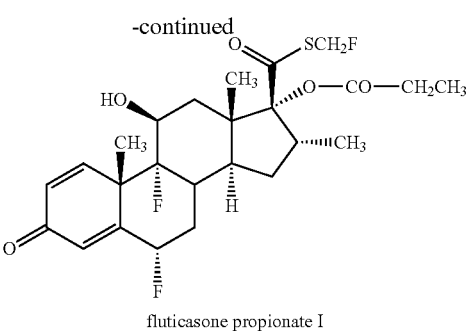

fluticasone propionate I

Step (a): Conversion of Thioalkyl Intermediates III into Thioalkyl Intermediates II According to the present invention there is provided a process for the preparation and purification of thioalkyl intermediates II, useful in the synthesis of steroidal 17β-carboxylic thioates such as fluticasone propionate I. In a preferred embodiment, the process comprises the use of a radical inhibitor and/or an antioxidant. In another preferred embodiment, the process comprises the use of a novel and selective solvent system for crystallisation.

Fluticasone propionate I of very high quality is required, because this compound is usually administered in special dosage form preparations, such as dry powder inhaler/metered dose formulations etc.

Thioalkyl compounds II are a key intermediate for the synthesis of fluticasone propionate I. Pure thioalkyl compounds II must be used in the synthesis of fluticasone propionate I, because polar as well as non-polar impurities, which are present from previous synthetic steps, are difficult to remove from fluticasone propionate I, even by multiple crystallisations and column chromatography.

It has now been surprisingly found that the use of radical inhibitors and/or antioxidants controls the formation of non-polar dimer impurities, even when the exchange reaction of step (a), for example chloro to bromo conversion, was extended further for completion to avoid the subsequent presence of traces of thioalkyl intermediate III in fluticasone propionate I. In addition, the use of these additives allowed lengthening the reaction time without any adverse effect on the quality of thioalkyl intermediate II.

It has also now been found that the purification of thioalkyl compounds II, using a novel and selective solvent system, can be used to control all impurities in general and non-polar dimer impurities in particular, prior to the fluorine exchange reaction (b) to obtain fluticasone propionate I of high purity.

The process of the present invention was found to always provide thioalkyl compounds II with a dimer impurity content of less than 0.10%, whereas the prior art processes afforded thioalkyl compounds II and fluticasone propionate I containing as much as 2.0% (typically 0.10% to 1.5%) of dimer impurities along with other non-polar impurities. Fluticasone propionate I, prepared using the thioalkyl compounds II prepared using the process of the present invention, was always found to have the quality required by the EP 5.0 and USP 29 specifications.

The key intermediates, thioalkyl compounds II, were prepared from flumethasone by following the chemistry disclosed by Finklestein (Journal of Medicinal Chemistry, 1994, vol. 37, no. 22, pages 3717ff).

Conversion of Chloromethyl Ester 5 into Iodomethyl Ester 6

Initial efforts to synthesise iodomethyl ester 6 were based on Finklestein conditions (Journal of Medicinal Chemistry, 1994, vol. 37, no. 22, pages 3717ff), i.e. sodium iodide in dry acetone. Chloromethyl ester 5 was reacted with sodium iodide (4.0 eq) in acetone (20 vol) at 55-60° C. for 5.5 to 24 hours. It was observed that the reaction was fast initially, with ~75% of the conversion being complete within the first 3 hours. After 3 hours, the reaction became very sluggish and a non-polar impurity (confirmed to be a dimer impurity by comparison of the RRT in the HPLC analysis using the method described in EP 5.0) started to build up. By the time the amount of starting chloromethyl ester 5 was reduced below 5% (HPLC % area), the amount of the non-polar dimer impurity had increased up to the tune of ~2-4% (HPLC % area).

The two basic problems associated with this conversion were:

The conversion was not complete even after prolonged continuation of the reaction at 60° C.

The simultaneous generation of the non-polar dimer impurity.

Neither a change of solvent (dimethylacetamide instead of acetone), nor a change of mode of addition (lotwise addition of chloromethyl ester 5), nor a use of different activators (Lewis acids such as $ZnCl_2$ and $ZnBr_2$, nor a use of different iodinating agents (LiI, KI and iodine), nor a use of various temperature conditions (25° C. to 65° C.) provided any promising results with respect to a reduction in reaction duration or a reduction in the formation of the non-polar impurity.

It was surprisingly found that when the conversion was attempted in the presence of a radical inhibitor with an antioxidant, the formation of oxidative impurities as well as non-polar dimer impurities could be controlled and minimized.

Various radical inhibitors, such as methylhydroquinone, bis(4-methoxy-3-tert-butyl-5-methyl-phenyl)sulphide, cyclohexene, L-cysteine, N,N-dimethylglycine, sorbic acid, and hydroquinone, were examined for their efficiency. Also, a number of antioxidants, such as ascorbic acid, potassium metabisulphite, sodium metabisulphite, sodium thiosulphate, butylated hydroxyanisole, and butylated hydroxytoluene, were checked for the effective control of the oxidative degradation. A systematic study was undertaken to identify the best radical inhibitor or the best antioxidant or the best combination of these two.

It was found that out of various combinations, hydroquinone as radical inhibitor and butylated hydroxytoluene (BHT) as antioxidant exhibited the best and most consistent control over the non-polar dimer impurity. Without wishing to be bound by theory, it is believed that this is due to trapping the radical responsible for dimerisation and to minimizing the oxidative dimerisation.

The use of hydroquinone and butylated hydroxytoluene gave good reproducibility and consistency with respect to control over the non-polar dimer impurity up to a 50 g scale. The amount of non-polar dimer impurity was not more than 0.5% (earlier this impurity was up to 36%). The results of the study of radical inhibitors and antioxidants are summarised in Table 1.

TABLE 1

| Exp no. | Reaction conditions | % Yield (w/w) | HPLC purity (area %) of iodomethyl ester 6 and non-polar impurity |
|---|---|---|---|
| Exp-1 | dry acetone (20 vol), NaI (4.0 eq), chloro-methyl ester 5, BHT, hydroquinone, 60-62° C., 48 hours, aqueous NaHCO$_3$ (5% w/v) | 70 | ester 6: 97.12 non-polar imp: 0.52 |
| Exp-2 | same as above | 75 | ester 6: 96.91 non-polar imp: 0.44 |
| Exp-3 | same as above | 81 | ester 6: 97.01 non-polar imp: 0.12 |
| Exp-4 | same as above | 76 | ester 6: 96.87 non-polar imp: 0.23 |
| Exp-5 | same as above | 85 | ester 6: 96.90 non-polar imp: 0.47 |
| Exp-6 | same as above | 81 | ester 6: 97.01 non-polar imp: 0.12 |

Hence, the presence of a radical inhibitor with an antioxidant can successfully drive the conversion of thioalkyl compounds III to thioalkyl compounds II to completion with improved purity and minimum formation of non-polar impurities.

Purification of Iodomethyl Ester 6

The use of a radical inhibitor (such as hydroquinone) and an antioxidant (such as BHT) controls the formation of the non-polar dimer impurity significantly and reduces it below 0.5%. In addition, it was surprisingly found that there was also an increase in the purity of thioalkyl compounds II to more than 95% (HPLC).

It was also noticed that this non-polar dimer impurity, which was the manifestation of oxidative/radical coupling, increased (up to 1.0%) during conversion of thioalkyl compounds II to fluticasone propionate I using silver fluoride. It is believed that some silver oxide generated during the course of the reaction may be responsible for this increase in the non-polar dimer impurity.

To meet the stringent limits for the non-polar dimer impurities 11 and 12 (no more than 0.2%), a purification methodology was developed for controlling these impurities within the acceptable level even after conversion into fluticasone propionate I.

The poor solubility of thioalkyl compounds II in most polar as well as non-polar solvents, like acetone, DMAc, DMF, cyclohexane, tetrahydrofuran, methanol, ethyl acetate etc, even at higher temperatures of 65-110° C. and in higher solvent proportions (up to 100 volume of solvent) made the task of purification even more challenging.

It was found that crystallisation methodology was the best-suited method for purification, due to intrinsic limitations of chromatographic purification with respect to scale up and commercial manufacturing.

A novel crystallisation system comprising acetic acid and ethyl acetate (20:10 v/v) was discovered for purification. The crystallisation of thioalkyl compounds II using acetic acid and ethyl acetate (20:10 v/v) at 80-85° C. surprisingly reduced the amount of the non-polar impurity to less than 0.10% consistently with 80-85% w/w yield. Also, most of the other known/unknown impurities were reduced to ~0.15%.

Thioalkyl compounds II, purified with this novel solvent system, afforded fluticasone propionate I conforming to stringent EP/USP specifications.

In addition, the uncommon solvent system of acetic acid/ethyl acetate used for the purification of thioalkyl compounds II also helped to achieve the required impurity profile for fluticasone propionate I on a larger scale consistently, especially with respect to the non-polar dimer impurity.

It was further found that the process of the present invention is insensitive to scale, i.e. reproducible on a larger scale and convenient for commercial manufacturing.

Table 2 illustrates the results.

TABLE 2

| Exp no. | Reaction conditions | % Yield (w/w) | HPLC purity (area %) of purified iodomethyl ester 6 and non-polar impurity |
|---|---|---|---|
| Exp-1 | acetic acid (20 vol) and ethyl acetate (10 vol) at 80-85° C., chilling to 0-5° C., 1 hour | 81 | ester 6: 99.12<br>non-polar imp: 0.04 |
| Exp-2 | same as above | 81 | ester 6: 99.56<br>non-polar imp: 0.06 |
| Exp-3 | same as above | 82 | ester 6: 99.01<br>non-polar imp: 0.07 |
| Exp-4 | same as above | 88 | ester 6: 98.99<br>non-polar imp: 0.05 |
| Exp-5 | same as above | 87.5 | ester 6: 99.19<br>non-polar imp: 0.06 |

Step (b): Conversion of Thioalkyl Intermediates II into Fluticasone Propionate I The synthesis of the present invention of steroidal 17β-carboxylic thioates, such as fluticasone propionate I, involves a novel combination of soluble mixed fluorides, which introduce fluorine by displacing an appropriate leaving group, for example, a chloro, bromo, iodo, benzenesulphonyl, p-toluenesulphonyl(tosyl), methylsulphonyl(mesyl), trifluoromethanesulphonyl(triflate), or acetate group. The use of soluble mixed fluorides and selected experimental conditions strictly controls the formation of polar as well as non-polar impurities associated with the processes disclosed in the prior art. The reaction of the present invention can be performed in solvents like acetonitrile, tetrahydrofuran (THF), ethyl acetate, dimethylformamide, dimethylacetamide, and combinations of ethyl acetate and acetonitrile, benzonitrile or propionitrile. The solvent acetonitrile gave the best results with respect to conversion and impurity profile.

It was surprisingly found that due to these improvements fluticasone propionate I was obtained in very high quality and in good yield (more than 80%), which is very much required because fluticasone propionate I is usually administered in special dosage form preparations, such as dry powder inhaler/metered dose formulations etc. Besides these advantages, the process of the present invention uses non-hazardous and environmentally friendly fluorinating agents and offers cost advantages, since it eliminates the use of halofluoromethanes and chromatographic purification, thereby making the process eco-friendly and economical.

The process of the present invention has the following preferred features:

A mixture of soluble fluorides, for example a mixture of silver fluoride and calcium fluoride, is used for selective fluorination.

A solution of mixed fluorides, for example in acetonitrile, provides the stoichiometric amount of fluoride required for complete conversion and avoids other competing fluorination reactions.

The homogeneous nature of the reaction helps to achieve a reproducible and consistent yield and purity of the product.

The minimum waste of mixed fluorides can be easily recovered and destroyed for waste stream purposes.

The use of stoichiometric fluoride allows for convenient work up procedures and easy isolation methods without the need for any chromatographic purification.

The application of the procedure described in J. Med. Chem., 1994, vol. 37, no. 22, page 3717ff, i.e. treatment with silver fluoride, gave fluticasone propionate I in poor quality (65-70% HPLC purity following the EP/USP method of analysis) and in miserable yield (~40% molar). The use of different fluorinating reagents, such as TBAF and $SbF_5$, also did not yield good results.

Surprisingly, it was found that there was a significant improvement in quality, when a mixture of fluorides (silver fluoride adsorbed on calcium fluoride) was used for the selective fluorination. For instance, the HPLC purity was improved to 88-93% from 60-65% obtained in earlier experiments.

Even more surprisingly, it was found that when a solution of silver fluoride was used as fluorinating reagent, the HPLC purity was further improved to 94%.

The above two modifications, i.e. the use of mixed fluorides and the use of silver fluoride in a solution, independently resulted in a significant improvement in the fluticasone propionate I quality. Indeed, when these two modifications were combined, the HPLC purity of fluticasone propionate I increased to more than 98-99%.

This combination proved to be very effective in controlling the formation of impurities during the reaction as well as being selective in fluorinating at C-17 bearing a halogen (iodine). On further purification (crystallisation from alcoholic solvents), the process of the present invention resulted in fluticasone propionate I conforming to the EP as well as the USP specification in good yield.

The results of various experimental modifications with respect to the quality and yield of fluticasone propionate I are summarized below:

1. The use of different solvents, for example acetonitrile, tetrahydrofuran (THF), ethyl acetate, dimethylformamide, dimethylacetamide, and combinations of ethyl acetate and acetonitrile, benzonitrile or propionitrile, and the mode of addition of silver fluoride gave fluticasone propionate I in 50% molar yield with HPLC purity ranging from 64-75%.
2. Changing the work up procedure and optimising the volume of the solvent (acetonitrile) improved the HPLC purity of fluticasone propionate I to 82-85%.
3. The use of non-dissolved potassium fluoride, caesium fluoride, antimony fluoride, and tetrabutyl ammonium fluoride did not give the required quality of fluticasone propionate I as compared to silver fluoride or a combination of calcium fluoride and silver fluoride.
4. The use of a combination of fluorides, i.e. calcium fluoride and silver fluoride, with acetonitrile as a solvent gave the best results for the fluorination reaction.

Preliminary Experiments—Effect of Silver Fluoride Solution

The use of iodo compound 6 and a silver fluoride solution gave very good HPLC purity (HPLC 94%) and a desired impurity profile. The major disadvantage of the use of a silver fluoride solution was the prolonged reaction duration (75 hour) and the fact that traces of compound 6 remained as unreacted starting material. Compound 6 was difficult to remove subsequently.

TABLE 3

| Exp no. | Reaction conditions | % Yield (w/w) | HPLC purity (area %) of fluticasone propionate I |
|---|---|---|---|
| Exp-1 | solution of silver fluoride (15.0 eq), at 0-5° C., more than 75 hour, no distillation of acetonitrile | 40 | 90.78 |

TABLE 3-continued

| Exp no. | Reaction conditions | % Yield (w/w) | HPLC purity (area %) of fluticasone propionate I |
|---|---|---|---|
| Exp-2 | same as above | 40 | 90.10 |
| Exp-3 | same as above | 50 | 92.10 |
| Exp-4 | same as above | 40 | 94.12 |

The formation of some specific impurities from the initiation of the reaction was observed in all of the above experiments. It was therefore concluded that these impurities should be controlled at the initiation stage of the reaction, which is the displacement of the iodo or other suitable leaving group by fluorine. It was decided to use a solution of mixed fluorides due to the encouraging purity obtained in experiment 4 in Table 3, using the above procedure.

Combinations of fluorinating agents, such as potassium fluoride, caesium fluoride, antimony fluoride, tetrabutyl ammonium fluoride and calcium fluoride with silver fluoride were examined with different reaction conditions. The results showed that the best fluorinating agent combination was silver fluoride and calcium fluoride.

A solution of silver fluoride (2 eq) and calcium fluoride (4 eq) was prepared using acetonitrile as preferred solvent at 25-90° C. followed by filtration to remove black metallic impurities. Application of the above-mentioned solution was a turning point for the specific conversion of compound 6 to fluticasone propionate I. The reaction was selective, although a bit sluggish at the beginning, due to the controlled reactivity of the mixed fluoride in soluble form and due to the homogeneous nature of the reaction. After 36 hours of stirring, the reaction was driven to completion by the addition of a further 2 eq of silver fluoride and stirring was continued for a further 12 hours. The formation of both, impurities and oxidation products, was successfully controlled as the silver salts were removed as previously by filtration.

The above modification gave very good results. The HPLC purity of crude fluticasone propionate I was increased to more than 97-98% from 88-93%, and the yield was increased to 55-60% w/w from 30-40% w/w obtained in earlier conditions.

The quality of the product obtained using the above experimental conditions also complied with the pharmacopoeial limits, with only one crystallisation from an alcoholic solvent. During the crystallisation, polar as well as non-polar impurities were reduced to pharmacopoeial acceptance levels when analyzed under stringent analytical conditions (EP/USP).

Example A

A solution of mixed fluorides was obtained by refluxing silver fluoride (10.0 eq) and calcium fluoride (10.0 eq) in acetonitrile at 90-95° C. for 4 hours, followed by filtration. Compound 6 was charged at −10 to −15° C. into the solution obtained and the reaction mixture was stirred for 36 hours at −10 to −15° C. Then further silver fluoride (2.0 eq) was added and the reaction mixture was stirred for a further 12 hours at −10 to −15° C. Crude fluticasone propionate I was isolated by aqueous extraction work up using ethyl acetate, $Na_2CO_3$, 2M HCl and water. Distillation of the ethyl acetate, followed by swapping with diisopropyl ether gave colourless fluticasone propionate I. By following this procedure, crude fluticasone propionate I was obtained with more than 98% HPLC purity consistently (Table 4).

TABLE 4

| Exp no. | Reaction conditions | % Yield (w/w) | HPLC purity (area %) of crude fluticasone propionate I |
|---|---|---|---|
| Exp-1 | acetonitrile filtrate of AgF (10.0 eq) and $CaF_2$ (10.0 eq), S-iodo compound 6, stirring at −10 to −15° C. for 36 hours, AgF (2.0 eq), stirring at −10 to −15° C. for further 12 hours | 60 | 98.15 |
| Exp-2 | same as above | 60 | 99.30 |

Example B

Fluticasone propionate I obtained from the above example was further crystallised using methanol (55 vol) at 60-65° C. The clear solution was treated with activated carbon and then filtered. By chilling the resulting solution to 0 to −5° C. for maximum isolation, pure product was isolated. This was dried under reduced pressure at 50-55° C. This gave fluticasone propionate I with more than 99% HPLC purity and conforming to the EP 5.0 and USP 29 specifications. The non-polar dimeric impurities (impurities H and I in EP 5.0; impurities D and E in USP 29) were significantly below (~0.10%) the specified pharmacopoeial limit (0.2% in EP 5.0, 0.3% in USP 29), see Table 5.

TABLE 5

| Exp no. | Crystallisation solvents and conditions | % Yield (w/w) | HPLC purity (area %) of purified fluticasone propionate I and RRT of impurities wrt EP 5.0/USP 29 |
|---|---|---|---|
| Exp-1 | Methanol (55 vol), reflux at 60-65° C., activated carbon, chilling to 0 to −5° C. | 71 | Related substances as per EP 5.0 fluticasone propionate I: 99.52<br>Impurity C: 0.10<br>Impurity F: 0.15<br>Impurity G: 0.15<br>Related substances as per USP 29<br>Imp C: 0.09 (limit: 0.20)<br>Imp E: 0.16 (limit: 0.20)<br>Unknown (Imp F as per EP): 0.10 (limit: 0.10)<br>Peak Purity: 99.56% |
| Exp-2 | same as above | 71 | Related substances as per EP 5.0 fluticasone propionate I: 99.58<br>Impurity C: 0.09<br>Impurity F: 0.16<br>Impurity G: 0.17<br>Related substances as per USP 29<br>Imp C: 0.10 (limit: 0.20)<br>Imp E: 0.03 (limit: 0.20)<br>Unknown (Imp F as per EP): 0.08 (limit: 0.10)<br>Peak Purity: 99.78% |

EXAMPLES

Example 1

Preparation of Iodomethyl Ester 6 from Chloromethyl Ester 5

Sodium iodide (4.0 eq) was charged to acetone (20 vol) under stirring. Butylated hydroxytoluene (BHT) (1.0 eq) and hydroquinone (1.0 eq) were added to the stirred suspension of sodium iodide at 25-30° C. The reaction mixture was stirred for 30 minutes. Chloromethyl ester 5 (1.0 eq) was added to this stirred suspension and the reaction mixture was refluxed for 24 hours at 60-65° C. After completion of the reaction, the product was isolated by distillation of acetone and precipitation by adding 5% w/v solution of NaHCO$_3$. The crude iodomethyl ester 6 was filtered, washed with water (3×10 vol) and dried under reduced pressure (~100 mm of Hg) at 55-60° C. for 4 hours. Yield: 75-85% w/w. HPLC purity: 96-97%.

Example 2

Purification of Iodomethyl Ester 6

The crude iodomethyl ester 6 from example 1 was dissolved in a solvent system of acetic acid (20 vol) and ethyl acetate (10 vol) at 85° C., then gradually cooled to 25-30° C. and then 0-5° C. and stirred further for 1 hour. The off-white crystalline product separated. Iodomethyl ester 6 was filtered, washed with 5% NaHCO$_3$ (10 vol) and dried under reduced pressure (~100 mm of Hg) at 55-60° C. for 4 hours. Yield: 75-85% w/w. HPLC purity: more than 99%.

Example 3

Conversion of Purified Iodomethyl Ester 6 to Fluticasone Propionate I

A solution of mixed fluorides was obtained by refluxing silver fluoride (10.0 eq) and calcium fluoride (10.0 eq) in acetonitrile at 90-95° C. for 4 hours. The purified iodomethyl ester 6 from example 2 was charged into the solution of mixed fluorides at −10 to −15° C. and stirred for 48 hours. Crude fluticasone propionate I was isolated by aqueous extractive work up using ethyl acetate, Na$_2$CO$_3$, 2M HCl and water. Distillation of ethyl acetate, followed by swapping with diisopropyl ether gave colourless fluticasone propionate I, which was dried under reduced pressure (~100 mm of Hg) at 55-60° C. for 4 hours. Yield: 75-85% w/w. HPLC purity: more than ~97%.

Example 4

Purification of Fluticasone Propionate I

Crude fluticasone propionate I from example 3 was crystallised using methanol (55 vol) at 60-65° C. The clear solution was treated with activated carbon and then filtered. The resulting solution was chilled to 0 to −5° C. and pure product was isolated, which was dried under reduced pressure at 50-55° C. Yield: 70-75% w/w. HPLC purity: see Table 5. The fluticasone propionate I thus obtained was always consistent with the EP 5.0 and USP 29 specifications.

It will be understood that the present invention has been described above by way of example only. The examples are not intended to limit the scope of the invention. Various modifications and embodiments can be made without departing from the scope and spirit of the invention, which is defined by the following claims only.

The invention claimed is:
1. A process of preparing S-fluoromethyl-6α,9α-difluoro-11β-hydroxy-16α-methyl-17α-propionyloxy-3-oxo-androsta-1,4-diene-17β-carbothioate I

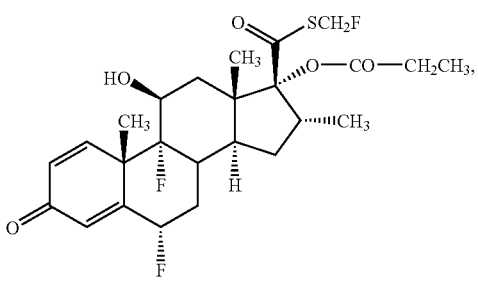

comprising using soluble mixed fluorides to fluorinate a compound II

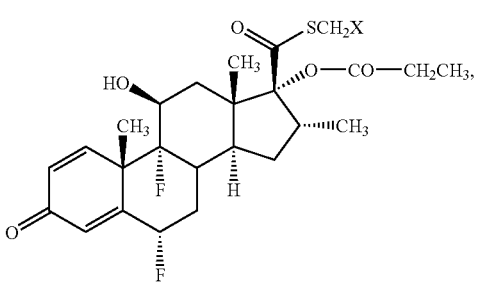

wherein X is a leaving group.

2. The process of claim 1, wherein the leaving group X is:
  (a) a chloro, bromo, iodo, benzenesulphonyl, p-toluenesulphonyl(tosyl), methylsulphonyl(mesyl), trifluoromethanesulphonyl(triflate), or OCOCH$_3$ group; or
  (b) iodo.

3. The process of claim 1, wherein the soluble mixed fluorides:
  (a) are selected from potassium fluoride, caesium fluoride, antimony fluoride, tetrabutyl ammonium fluoride, calcium fluoride, silver fluoride, bis(2-methoxyethyl)aminosulphur trifluoride (DEOXO-FLUOR®), diethylaminosulphur trifluoride (DAST®), and hexafluoropropyldiethylamine (MEC-81®); or
  (b) are selected from potassium fluoride, caesium fluoride, antimony fluoride, tetrabutyl ammonium fluoride, calcium fluoride, and silver fluoride; or
  (c) comprise silver fluoride and at least one other fluoride; or
  (d) comprise or are silver fluoride and calcium fluoride; or
  (e) are a solution of soluble mixed fluorides in an organic solvent; or
  (f) are a solution of soluble mixed fluorides in an organic solvent, and wherein the solution of soluble mixed fluorides is prepared by heating the soluble mixed fluorides in the organic solvent at a temperature of 25-95° C.; or
  (g) are a solution of silver fluoride and calcium fluoride in an organic solvent; or
  (h) are a solution of silver fluoride and calcium fluoride in an organic solvent, and wherein the solution of soluble mixed fluorides is prepared by heating the soluble mixed fluorides in the organic solvent at a temperature of 25-95° C.

4. The process of claim 3, wherein the organic solvent:
  (a) is selected from acetonitrile, tetrahydrofuran, ethyl acetate, dimethylformamide, dimethylacetamide, and a combination of ethyl acetate and acetonitrile, benzonitrile or propionitrile; or
  (b) comprises or is acetonitrile.

5. The process of claim 1, wherein:
  (a) the use of the soluble mixed fluorides results in selective and controlled fluorination of the —CO—SCH$_2$X group of compound II; or
  (b) the process further comprises the step of crystallising compound I from an alcohol.

6. The process of claim 1, wherein:
  (a) the compound I obtained comprises less than 0.4% of dimer impurities 17,17'-(disulphanediyldicarbonyl)bis(6α,9α-difluoro-11β-hydro-16α-methyl-3-oxo-androsta-1,4-diene-17α-yl)dipropionate 11 and 17,17'-(trisulphanediyldicarbonyl)bis(6α,9α-difluoro-11β-hydroxy-16α-methyl-3-oxo-androsta-1,4-diene-17α-yl)dipropionate 12; or
  (b) the HPLC purity of the compound I obtained is greater than 97%; or
  (c) the yield of the compound I obtained is greater than 60%.

7. The process of claim 1, wherein prior to fluorination compound II is crystallised using a solvent system comprising a polar and a non-polar solvent.

8. The process of claim 7, wherein the solvent system comprises:
  (a) ethyl acetate, butyl acetate, methyl acetate, isopropyl acetate, methanol, acetone, THF, dimethylformamide, dimethylacetamide, methyl acetate/formic acid, methyl acetate/acetic acid, ethyl acetate/acetic acid, isopropyl acetate/acetic acid, butyl acetate/acetic acid, ethyl acetate/propionic acid, or ethyl acetate/butyric acid; or
  (b) ethyl acetate and acetic acid.

9. The process of claim 7, wherein:
  (a) the compound II obtained comprises less than 0.4% of dimer impurities 17,17'-(disulphanediyldicarbonyl)bis(6α,9α-difluoro-11β-hydroxy-16α-methyl-3-oxo-androsta-1,4-diene-17α-yl)dipropionate 11 and 17,17'-(trisulphanediyldicarbonyl)bis(6α,9α-difluoro-11β-hydroxy-16α-methyl-3-oxo-androsta-1,4-diene-17α-yl)dipropionate 12; or
  (b) the HPLC purity of the compound II obtained is greater than 95%; or
  (c) the yield of the compound II obtained is greater than 60%.

10. The process of claim 1, wherein prior to fluorination compound II is prepared by converting a compound III

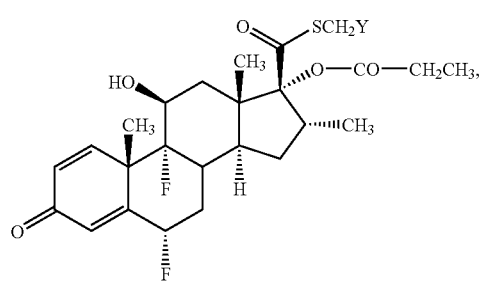

wherein Y is another leaving group, into compound II in the presence of a radical inhibitor or an antioxidant or both.

11. The process of claim 10, wherein the leaving group Y is:
  (a) a chloro, bromo or hydroxyl group; or
  (b) chloro.

12. The process of claim 10, wherein:
  (a) the radical inhibitor is selected from methylhydroquinone, bis(4-methoxy-3-tert-butyl-5-methyl-phenyl)sulphide, cyclohexene, L-cysteine, N,N-dimethylglycine, sorbic acid and hydroquinone; or
  (b) the radical inhibitor is hydroquinone; or
  (c) the antioxidant is selected from ascorbic acid, potassium metabisulphite, sodium metabisulphite, sodium thiosulphate, butylated hydroxyanisole and butylated hydroxytoluene; or
  (d) the antioxidant is butylated hydroxytoluene; or
  (e) the conversion is carried out in presence of hydroquinone and butylated hydroxytoluene.

13. The process of claim 10, wherein:
  (a) the compound II obtained comprises less than 0.5% of dimer impurities 17,17'-(disulphanediyldicarbonyl)bis(6α,9α-difluoro-11β-hydroxy-16α-methyl-3-oxo-androsta-1,4-diene-17α-yl)dipropionate 11 and 17,17'-(trisulphanediyldicarbonyl)bis(6α,9α-difluoro-11β-hydroxy-16α-methyl-3-oxo-androsta-1,4-diene-17α-yl)dipropionate 12; or
  (b) the HPLC purity of the compound II obtained is greater than 95%; or
  (c) the yield of the compound II obtained is greater than 60%.

14. The process of claim 7, wherein prior to crystallisation compound II is prepared by converting a compound III

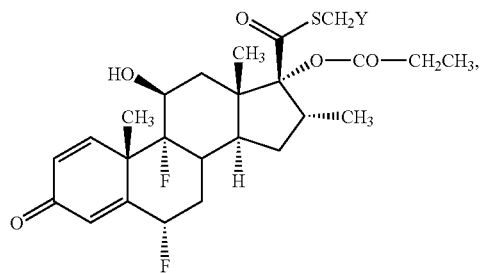

wherein Y is another leaving group, into compound II in the presence of a radical inhibitor or an antioxidant or both.

15. The process of claim 14, wherein the leaving group Y is:
  (a) a chloro, bromo or hydroxyl group; or
  (b) chloro.

16. The process of claim 14, wherein:
  (a) the radical inhibitor is selected from methylhydroquinone, bis(4-methoxy-3-tert-butyl-5-methyl-phenyl)sulphide, cyclohexene, L-cysteine, N,N-dimethylglycine, sorbic acid and hydroquinone; or
  (b) the radical inhibitor is hydroquinone; or
  (c) the antioxidant is selected from ascorbic acid, potassium metabisulphite, sodium metabisulphite, sodium thiosulphate, butylated hydroxyanisole and butylated hydroxytoluene; or
  (d) the antioxidant is butylated hydroxytoluene; or
  (e) the conversion is carried out in presence of hydroquinone and butylated hydroxytoluene.

17. The process of claim 14, wherein:
(a) the compound II obtained comprises less than 0.5% of dimer impurities 17,17'-(disulphanediyldicarbonyl)bis(6α,9α-difluoro-11β-hydroxy-16α-methyl-3-oxo-androsta-1,4-diene-17α-yl)dipropionate 11 and 17,17'-(trisulphanediyldicarbonyl)bis(6α,9α-difluoro-11β-hydroxy-16α-methyl-3-oxo-androsta-1,4-diene-17α-yl)dipropionate 12; or (b) the HPLC purity of the compound II obtained is greater than 95%; or (c) the yield of the compound II obtained is greater than 60%.

* * * * *

UNITED STATES PATENT AND TRADEMARK OFFICE
CERTIFICATE OF CORRECTION

PATENT NO. : 8,344,168 B2
APPLICATION NO. : 12/329790
DATED : January 1, 2013
INVENTOR(S) : Gore et al.

Page 1 of 1

It is certified that error appears in the above-identified patent and that said Letters Patent is hereby corrected as shown below:

Title Page, Item (73), Assignee:

PTO
"Generics (UK) Limited (GB)"

Should Be
--Generics [UK] Limited (GB)--

In the Claims:

| Column | Line | PTO | Should Be |
|---|---|---|---|
| 25 | 17 | "(6α, 9α-difluoro-11β-hydro-16α-methyl-3-oxo-an" | --"(6α, 9α-difluoro-11β-hydroxy-16α-methyl-3-oxo-an-- |

Signed and Sealed this
Twelfth Day of November, 2013

Teresa Stanek Rea
*Deputy Director of the United States Patent and Trademark Office*